United States Patent

Härröd et al.

Patent Number: 5,962,711
Date of Patent: Oct. 5, 1999

[54] HYDROGENATION OF SUBSTRATE AND PRODUCTS MANUFACTURED ACCORDING TO THE PROCESS

[75] Inventors: Magnus Härröd, Alingsas; Poul Møller, Aarhus, both of Sweden

[73] Assignee: Poul Moller Ledelses- OG Ingeniorradgivning APS, Arhus, Denmark

[21] Appl. No.: 08/765,622

[22] PCT Filed: Jul. 3, 1995

[86] PCT No.: PCT/SE95/00824

§ 371 Date: Dec. 27, 1997

§ 102(e) Date: Dec. 27, 1997

[87] PCT Pub. No.: WO96/01304

PCT Pub. Date: Jan. 18, 1996

[30] Foreign Application Priority Data

Jul. 1, 1994 [SE] Sweden .................................. 9402362

[51] Int. Cl.⁶ ..................................................... C07C 51/36
[52] U.S. Cl. .......................... 554/145; 554/141; 554/143; 554/144; 568/876; 568/880; 423/587
[58] Field of Search ...................... 589/141, 143, 589/144, 145; 568/876, 880; 423/587

[56] References Cited

U.S. PATENT DOCUMENTS 3,969,382  7/1976  Zosel ....................... 260/409

FOREIGN PATENT DOCUMENTS 4405029  8/1995  Germany .
9406738  3/1994  WIPO .
9522591  8/1995  WIPO .

OTHER PUBLICATIONS

Pickel et al. "Supercritical Fluid Sovents for Reactions", Proc. 3$^{rd}$ Int'l Symp. on Supercritical Fluids pp. 25–29 (1994).

Primary Examiner—Gary Geist
Assistant Examiner—Deborah D. Carr
Attorney, Agent, or Firm—Oppedahl & Larson LLP

[57] ABSTRACT

A typical traditional reactor for hydrogenation consists of a tank filled with a liquid and a gas and a small particle catalyst. The reaction is carried out at high pressures and high temperatures. Lack of gas on the catalyst surface limits the velocity of reaction. Much work has been done to increase the quantity of gas on the catalyst. It has not been possible to solve this problem effectively with the techniques of today. According to the invention an extra solvent is added to the reaction mixture. By bringing the whole mixture (solvent, substrate, hydrogen and reaction products) to super-critical or near-critical state, a substantially homogeneous mixture can be obtained. By this method it is possible to control the concentration of gas on the catalyst to the desired level. The velocity of reaction is thereby increased considerably. The hydrogenation reactions principally involved comprise hydrogenation of carbon-carbon double bonds (C=C) in lipids; hydrogenation of COOR to C—OH and HO—R to produce fatty alcohols; and direct hydrogenation of oxygen to hydrogen peroxide.

13 Claims, 1 Drawing Sheet

HYDROGENATION OF SUBSTRATE AND PRODUCTS MANUFACTURED ACCORDING TO THE PROCESS

This application is a 371 of PCT/SE95/00824 filed Jul. 3, 1995.

TECHNICAL FIELD OF THE INVENTION

The present invention relates to a process for the hydrogenation of a substrate, where hydrogen gas is mixed with the substrate in the presence of a catalyst and the reaction is carried out at certain reaction conditions of pressure, time and temperature. The hydrogenation reactions are mainly related to the hydrogenation of carbon-carbon double bonds (C=C) in lipids;
hydrogenation of COOR to C—OH and HO—R for the manufacturing of fatty alcohols; and the direct hydrogenation of oxygen to hydrogen peroxide.

BACKGROUND OF INVENTION

C=C in lipids.

The annual production of vegetable oils is about 90.million tons (Mielke 1992), of which about 20% are hardened (hydrogenated). Furthermore, about 2 million tons of marine oils are hydrogenated yearly. The production is spread over the whole industrialized world. Through the hydrogenation, hydrogen is added to the double bonds of the unsaturated fatty acids. The largest part of the oils is only partly hydrogenated. The desired conditions of melting and the desired consistency of the fats are thereby obtained, which are of importance for the production of margarine and shortening. The tendency to oxidation is reduced by the hydrogenation, and the stability of the fats is increased at the same time (Swern 1982).

In the future, the lipids may be modified by methods belonging to bio technology, especially gene technology, but hydrogenation will certainly remain.

A problem with the hydrogenation processes of today is, that new fatty acids are produced which to a great extent do not exist in the nature. They are often called trans fatty acids, but the double bonds change position as well as form (cis-trans) during the hydrogenation (Allen 1956, Allen 1986).

As a rule, trans fatty acids are desired from a technical and functional point of view (Swern 1982), but regarding health, their role is becoming more and more questionable (Wahle & James 1993).

A typical state of the art reactor for hydrogenation is a large tank (5 to 20 $m^3$) filled with oil and hydrogen gas plus a catalyst in the form of fine particles (nickel in powdery form). The reaction is carried out at a low pressure, just above atmospheric (0.5 to 5 bar), and high temperatures (130 to 210° C.). The hydrogen gas is thoroughly mixed into the oil, as this step restricts the reaction rate (Grau et al., 1988).

If the pressure of hydrogen gas is increased from 3 to 50 bar when soya oil is partially hydrogenated (iodine number at the start=135, at the end=70), the content of trans is reduced from 40 to 15%. The position isomerization is also reduced to a corresponding level (Hsu et al., 1989). These results are of no commercial interest, as these conditions enforce a replacement of the low pressure autoclaves by high pressure autoclaves.

According to the "half hydrogenation" theory, the concentration of activated H-atoms on the catalyst surface determines the number of double bonds being hydrogenated and deactivated without being hydrogenated respectively. A lack of activated H-atoms causes a trans- and position-isomerization (Allen 1956, Allen 1986). A lack of activated H-atoms can be the consequence of low solubility of $H_2$ in the oil, or of a bad catalyst (poisoned or inadequately produced). Thus, the "half hydrogenation" theory corresponds very well to the empirical results (Allen 1956; Allen 1986; Hsu et al., 1989).

It is possible to deodorize and hydrogenate an oil in the presence of $CO_2$ and hydrogen (Zosel 1976). Zosel describes in detail how to use $CO_2$ in order to deodorize the oil. However, it must be emphasized that Zosel does not give any hint, that $CO_2$ should have an influence on the hydrogenation process. Furthermore, Zosel does not touch on the cis/trans problem.

In the experiments of Zosel, the catalyst is surrounded by a liquid phase during the entire process. Zosel does not disclose the composition, but in the light of the other data, we estimate that the liquid phase consists of oil (about 95%), $CO_2$ (about 5%) and hydrogen (about 0.03%). This phase is far away from a supercritical condition. As a consequence, the velocity of reaction is limited by the concentration of hydrogen on the catalyst surface. The same applies to all traditional hydrogenation reactions where the catalyst is in the liquid phase as well. The velocity of hydrogenation in the experiments of Zosel is about 100 kg/$m^3$h, i.e. somewhat lower than in traditional hydrogenizing reactors.

FATTY ALCOHOLS.

Fatty alcohols and their derivatives are used in shampoo, detergent compositions and cosmetic preparations etc. The annual production is about 1 million tons. About 60% is based on petrochemicals, and about 40% is derived from natural fats and oils. The raw material for short chain fatty alcohols, $C_{12}$–$C_{14}$, is coco-nut oil and palm kern oil, whereas $C_{16}$–$C_{18}$ comes from tallow, palm oil or palm stearin (Kreutzer 1984, Ong et al., 1989).

It is theoretically possible to hydrogenate triglycerides, fatty acids and methylesters to fatty alcohols. A direct hydrogenation of triglycerides has not been developed commercially, because the glycerol will be hydrogenated as well and thus lost. A direct hydrogenation of fatty acids requires corrosion resistant materials and a catalyst resistant to acids (Kreutzer 1984). Lurgi has developed a hydrogenation process (the slurry process), where fatty acids are introduced and are quickly esterified with a fatty alcohol to a wax ester, and then the wax ester is hydrogenated (copper chromite, 285° C., 300 bar)(Buchhold 1983, Voeste Buchhold 1984, Lurgi 1994).

Most plants for the production of natural fatty alcohols are based on methyl esters as raw material. Saturated fatty alcohols are produced at a temperature of about 210° C. and a pressure of 300 bar using copper chromite as catalyst in a fixed bed reactor. Other catalysts as copper carbonate, nickel or copper and chromic oxide will also function (Mahadevan 1978, Monick 1979, Lurgi 1994). Unsaturated fatty alcohols are produced at about 300° C. and 300 bar, normally using zinc chromite as catalyst. There are also other catalysts which selectively hydrogenate the group COOR, leaving the C=C unimpaired (Klonowski et al., 1970; Kreutzer 1984).

The reaction is limited by the solubility of hydrogen in the liquid (Hoffman Ruthhardt 1993).

Davy Process Technology markets a gas phase process where methyl esters are hydrogenated to fatty alcohols (40 bar, 200 to 250° C., catalyst without chromium) (Hiles 1994).

A lot of work has been done to develop catalysts functioning with less energy (lower temperature, lower pressure). Another object has been to develop methods for a direct hydrogenation of triglycerides to fatty alcohols without a simultaneous hydrogenation of the glycerol (Hoffman Ruthhardt 1993).

HYDROGEN PEROXIDE.

Hydrogen peroxide is used in large quantities for bleaching, cleaning, as a disinfectant and as a raw material in industrial processes etc. Earlier, hydrogen peroxide was derived by an electrolytic process. Now, oxidation of substituted hydroquinone or 2-propanol is most widely used.

There are a lot of patents concerned with direct synthesis of hydrogen peroxide from oxygen and hydrogen. The reaction medium can be acidic organic solvents or water with organic solvents using noble metals, most often palladium, as catalyst (EP-B-0049806; EP-B-0117306; U.S. Pat. No. 4,336,239; EP-B-0049809).

It is preferred that the reaction medium is free from organic constituents because of problems with purification. Several patents use acidic water as the reaction medium (pH=1–2) with addition of halides, especially bromide and chloride (<1 mM) and with noble metals or mixtures of noble metals as catalysts (EP-A-0132294; EP-A-0274830; U.S. Pat. No. 4,393,038; DE-B-2655920; DE 4127918 A1).

The velocities of reaction which are disclosed are about 1 kg/m$^3$h, and the selectivity (mol hydrogen peroxide/mol hydrogen reacted) is about 75% (DE 4127918 A1).

According to theory, one can expect to obtain- high selectivity with high concentrations of oxygen and hydrogen on the catalyst surface (Olivera et al., 1994).

The object of the present invention is to obtain a very effective process for partial or complete hydrogenation of the substrates mentioned above.

According to the invention, this problem has been solved by mixing the substrate, hydrogen gas and solvent, and by bringing the whole mixture into a super-critical or near-critical state. This substantially homogeneous super-critical or near-critical solution is led over the catalyst, whereby the reaction products formed, i.e. the hydrogenated substrates, will also be a part of the substantially homogeneous super-critical or near-critical solution.

The solvent can be a saturated hydrocarbon or an unsaturated hydrocarbon which on hydrogenation gives a saturated hydrocarbon, e.g. ethane, ethene, propane, propene, butane, butene, or $CO_2$, dimethyl ether, "freons", $N_2O$, $N_2$, $NH_3$, or mixtures thereof.

Propane is a suitable solvent for many lipids. $CO_2$ is a suitable solvent for hydrogen peroxide and water.

The catalyst will be selected according to the reaction which is to be carried out. For a partial or complete hydrogenation of only C=C bonds, preferably a noble metal or nickel will be selected. For a selective hydrogenation of COOR to C—OH and HO—R, the catalyst would preferably be a zinc salt, e.g. zinc chromite. For a simultaneous hydrogenation of COOR to C—OH and HO—R and a hydrogenation of C=C, the preferred catalyst would be copper chromite, another salt of copper or copper free from chrome. For a partial hydrogenation of oxygen to hydrogen peroxide, the preferred catalyst would be a noble metal.

According to the invention, the concentration of hydrogen on the catalyst surface can be controlled to very high levels. The proportion of trans fatty acids in partially hydrogenated fatty products will be much lower according to the invention than by using conventional processes, where the product has been hydrogenated to the same level using the same catalyst. The hydrogenated products will preferably contain less than 10% trans fatty acids.

DETAILED DESCRIPTION OF THE INVENTION

Figure 1:
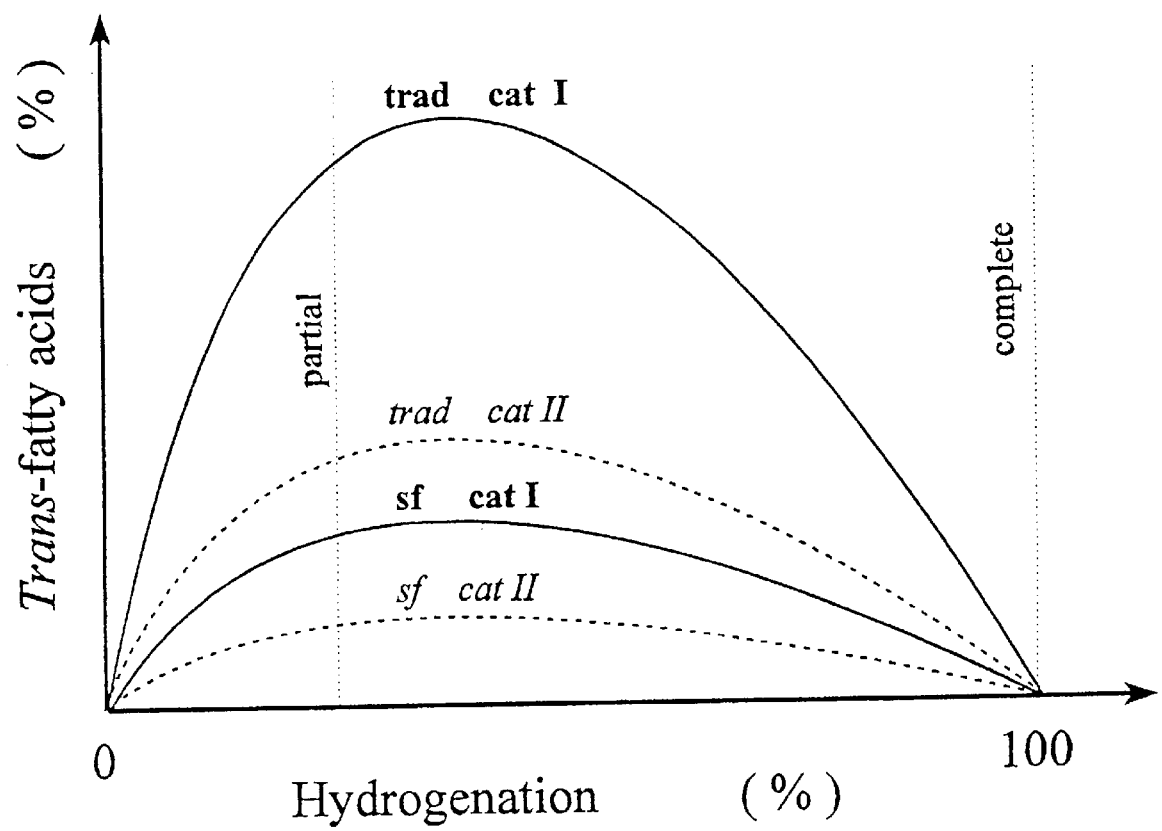
FIG. 1 is a diagram showing the percentage of trans fatty acids as a function of the degree of hydrogenation according to a traditional technique and according to the invention.

In a great number of hydrogenation processes, hydrogen gas is mixed with a liquid substrate and a fixed catalyst, e.g. in the hydrogenation of lipids. In certain cases the substrate can be a gas and the product a liquid, e.g. hydrogenation of oxygen to hydrogen peroxide and water. In both these cases, the velocity of reaction is limited by the concentration of gas on the catalyst surface. The reason is the transport resistances of the gas: between the gas phase and the liquid phase; through the liquid phase; and between the liquid phase and the catalyst.

In accordance with the present invention a solvent is added which completely dissolves the gas as well as the liquid, resulting in a substantially homogeneous mixture of hydrogen, substrate, product and solvent. This is possible, if the whole mixture is in a super-critical or near-critical state. The defition substantially homogeneous means, that the principal part of the gas is in the continuous phase which covers the catalyst surface. One method to confirm this is to observe the velocity of reaction, which increases dramatically when the continuous phase that covers the catalyst surface is substantially homogeneous.

VELOCITY OF REACTION.

According to the invention, the following transport resistances of the gas are reduced substantially: gas phase/liquid phase; through the liquid phase; and liquid phase/catalyst. The velocity of reaction thereby increases to a very high degree; from about 10 to about 1000 times. The consequence of this is that continuous reactors will be preferred compared to the batch reactors of to-day. The selectivity is also influenced to a very high degree.

SOLVENT.

In order to bring the whole mixture (hydrogen, substrate product and solvent) to super critical or near-critical state at appropriate pressures and temperatures, the solvent must dissolve substrate and product as much as possible.

Glycerides, fatty acids and many derivatives of fatty acids are completely miscible with super-critical propane (Peter et al., 1993). Propane can be used in any proportions together with food according to EU-regulations (Sanders 1993; EC 1984). Thus, propane is a very adequate solvent in reactions with lipids.

Water dissolves to a certain extent in $CO_2$ (King et al., 1992). Hydrogen peroxide dissolves more easily than water in $CO_2$. Thus, $CO_2$ is an appropriate solvent for direct synthesis of hydrogen peroxide. (For a thorough description of super-critical technology, see McHugh Krukonis 1986; Dohrn 1994).

CATALYSTS.

The catalysts which are used today in traditional processes can in principle also be used in super-critical processes. The catalyst may however be modified to optimize selectivity, velocity of reaction, length of life, filtering properties and pressure-drop.

QUALITY OF PRODUCT.

The invention enables new possibilities to control the hydrogen concentration at the catalyst. The velocity of reaction increases substantially. The selectivity can also be influenced in certain processes. By partial hydrogenation of edible oils, the content of trans fatty acids is of importance for the quality (see background of invention).

FIG. 1 illustrates in principle how the proportion of trans fatty acids changes during hydrogenation with two different catalysts, one catalyst according to a traditional technique and another according to the new super-critical technique. The new supercritical technique makes it possible to reduce the content of trans fatty acids in comparison with the traditional technique using the same catalyst and the same degree of hydrogenation. However, using different catalysts, the difference may be less.

In FIG. 1, "trad" means traditional process; "sf" means process with super critical fluid; and "cat" means catalyst.

CONDITIONS OF REACTION.

C=C in lipids.

I. Partial hydrogenation.

At partial hydrogenation, the reaction is interrupted at a certain iodine number, e.g. 60. The substrate, e.g. vegetable, animal or marine oil, and hydrogen are dissolved in a solvent, e.g. propane. The mixture is brought to a supercritical or a near-critical state. The substantially homogeneous mixture is brought into contact with a catalyst, e.g. palladium. The content of trans fatty acids in the final product is less than 10%. The optimal reaction condition may occure over a wide experimental range and this range can be described as follows:

|  | in general | preferably |
| --- | --- | --- |
| temperature | 0–250° C. | 20–200° C. |
| pressure | 10–350 bar | 20–200 bar |
| time of reaction | 0*–10 min | 1 μsec–1 min |
| solvent | 30–99.9 wt % | 40–99 wt % |

The solvent must dissolve the substrates at the concentrations used. The solvent can be ethane, ethene, propane, propene, butane, butene, $CO_2$, dimethyl ether, "freons", $N_2O$, $N_2$, $NH_3$ or mixtures of these gases. Preferred are propane, propene, butane, butene and dimethyl ether. Most preferred is propane.

| concentration of $H_2$ | 0*–3 wt % | 0.001–1 wt % |
| --- | --- | --- |
| concentr.substrate | 0.1–70 wt % | 1–60 wt % |

-type of substrate:

C=C in general. Glycerides are preferred (mono-, di-, triglycerides, galactolipids, phospholipids), also fatty acids or their derivatives (e.g. methyl- and ethyl-esters).

-catalysts noble metals: Pd, Pt, Os, . . . but also Ni.

(0* means very low values, below the lowest one under "preferably").

II. Complete hydrogenation.

At complete hydrogenation, all double bonds are hydrogenated and the iodine number is therefore near zero. The substrate, e.g. vegetable, animal or marine oil, and hydrogen are dissolved in a solvent, e.g. propane. The mixture is brought to a supercritical or near-critical condition, and the substantially homogeneous mixture is brought into contact with a catalyst, e.g. palladium.

The optimal conditions of reaction are wide and can be described in a similar way as for partial hydrogenation; the temperature is, however, somewhat higher than for partial hydrogenation (T is probably higher than $T_{crit}$).

FATTY ALCOHOLS.

The substrate, e.g. the triglyceride, the fatty acid or its derivative, and hydrogen are mixed together with a solvent, e.g. propane. The mixture is brought to a super-critical or a near-critical state, and the substantially homogeneous mixture is brought into contact with a catalyst. Different groups can be hydrogenated depending on the catalyst used (see below under "-catalyst").

The optimal reaction condition may occure over a wide experimental range and this range can be described as follows:

|  | in general | preferably |
| --- | --- | --- |
| temperature | 20–300° C. | 40–300° C. |
| pressure | 10–350 bar | 20–200 bar |
| time of reaction | 0*–10 min | 1 μsec–1 min |
| solvent | 30–99.9 wt % | 40–99 wt % |

The solvent must dissolve the substrates at the concentrations used. The solvent can be ethane, ethene, propane, propene, butane, butene, $CO_2$, dimethyl ether, "freons", $N_2O$, $N_2$, $NH_3$ or mixtures of these gases. Preferred are propane, propene, butane, butene, and dimethyl ether. Sometimes, it can be advantageous to use an entrainer. Most preferred is pure propane.

| concentration $H_2$ | 0*–3 wt % | 0.001–1 wt % |
| --- | --- | --- |
| concentr.substr. | 0.1–70 wt % | 1–60 wt % |

-type of substrate:

COOR in general. Preferred are fatty acids and their derivatives (e.g. methyl-ethyl- or wax esters), and also mono- di-, and tri-glycerides, but also galactolipids and phospholipids.

-catalyst:

a) selective hydrogenation of COOR, but not C=C or C—OH, e.g. zinc chromite or any other salt of zinc.

b) hydrogenation of both COOR and C=C, but not C—OH, e.g. copper chromite, copper free from chrome or any other salt of copper.

(0* means very low values, less than the lowest one under "preferably").

An example of suitable values at optimal conditions is:

substrate 10 wt %, propane about 90 wt %, hydrogen 0.2 wt %; the mixture is brought into contact with a bed of catalyst at 250° C. and 150 bar, and has an average contact time of 30 sec.

HYDROGEN PEROXIDE.

Oxygen and hydrogen are mixed in a solvent, e.g. $CO_2$. The mixture is brought to a super-critical or near-critical state, and the substantially homogeneous mixture is brought in contact with a catalyst. The solvent dissolves the reaction products, hydrogen peroxide and water. Thus, a substantially homogeneous mixture is maintained in the reactor.

The optimal reaction condition may occure over a wide experimental range and this range can be described as follows:

|  | in general | preferably |
|---|---|---|
| temperature | 10–200° C. | 20–10 0° C. |
| pressure | 10–350 bar | 30–300 bar |
| time of reaction | 0*–10 min | 1 μsec–1 min |
| solvent | 10–99.9 wt % | 60–99 wt % |

The solvent must dissolve water and hydrogen peroxide at the concentrations used. The solvent can be $CO_2$, $N_2$, $NH_3$, or mixtures of these gases. It may also be advantageous to use an entrainer. Pure $CO_2$ is probably the most suitable solvent.

| concentration $H_2$ | 0*–10 wt % | 0.1–3 wt % |
|---|---|---|
| concentration $O_2$ | 0.1–80 wt % | 1–30 wt % |

-catalyst:
  noble metals, e.g. Pd or mixtures of noble metals, e.g. Pd+Au
-reaction aids:
  halides, e.g. bromides or chlorides; these can be added in the preparation of the catalyst
(0* means very low values, less than the lowest under Y preferably")

The risk of explosion during some of the processing steps must be warned against.

Suitable proportions of the added constituents can be exemplified by: oxygen 3 wt %, hydrogen 0.1 wt % and $CO_2$ 96.9 wt %. The mixture is brought into contact with a catalyst of palladium at 35° C. and 200 bar; the average contact time is 0.1 sec.

EQUIPMENT AND ANALYTICAL METHODS

Equipment

Figure 2:
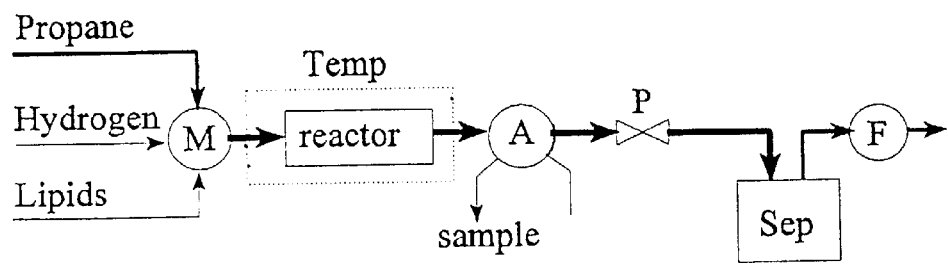
FIG. 2 is a flow sheet for a process according to the invention.

A flow sheet for the continuous reactor used, is illustrated in FIG. 2. In this figure "M" is a mixer, "Temp." a temperature controller, "A" a sampling device for analyses, "P" a pressure reduction valve, "Sep" a vessel for separation of gas/liquids and "F" a gas flow-meter. At room temperature a condensed gas, a non-condensable gas and a liquid were mixed according to the principles used by Pickel in a "Supercritical Fluid Chromatography" application (Pickel 1991). Pickel mixed CO2 nitrogen and a liquid entrainer. We mixed propane (l), hydrogen (g) and lipids (see M in FIG. 2). The same equipment can be used for the hydrogen peroxide experiments but in this case one add: $CO_2$ (l); oxygen+ hydrogen (g); reaction aids (l).

The mixture was heated to the desired reaction temperature and was brought into an HPLC tube filled with a catalyst powder (see Temp and Reactor in FIG. 2).

After the reactor samples were collected from the high pressure section using an HPLC valve (see A in FIG. 2 and Harrod et al 1994).

The pressure was reduced to atmospheric pressure and lipids and gases were separated (see P and Sep in FIG. 2). Then the gas flow was measured (see F in FIG. 2) The gasflow was controlled by the pressure-reduction valve (P in FIG. 2).

Analysis

The product quality was analysed using silver-ion-HPLC and gradient elution (Elfman Harröd 1995). This method is developed from an isocratic method (Adolf 1994). The kind (cis/trans) and the amount of the fatty acid methyl esters (FAME) was determine. From these data the iodine value (IV) was calculated.

The density was calculated from the Peng-Robinsson equation of state (Dohrn 1994).

EXAMPLES

Example 1

Partial hydrogenation of methylesters from rapeseed oil using a palladium catalyst.

Composition and amound of the inlet flow to the reactor:

|  | mole % | weight % | mg/min |
|---|---|---|---|
| propane | 99.92 | 99.7 | 3700 |
| hydrogen | 0.04 | 0.002 | 0.07 |
| FAME | 0.04 | 0.26 | 10 |

Reaction conditions:

| catalyst | 5% Pd on char coal (E 101 O/D 5% Degussa AG) |
|---|---|
| reactor volume | 0.007 ml |
| reaction time | 40 ms |
| temperature | 50° C. |
| pressure | 120 bar | productivity and product quality:

| productivity | 80 000 kg FAME/$m^3$ h |
|---|---|
| Iodine-value | reactor inlet = 110 |
|  | reactor outlet = 50 |
| FAME with trans | 10% of all FAME |

Comments

This example shows that a very high productivity (80 000 kg FAME/$m^3$ h) and a low content of trans-fatty acids (10%) can be attained at near-critical conditions. The results above is only an example. We do not claim that it is the optimal conditions for the process.

Others (Berben et al 1995) has minimized the trans-fatty acid content using the conventional technique. The productivity became much lower (700 kg triglycerides /$m^3$ h) and the content of the trans-fatty acids became much higher (34%).

Example 2

Complete hydrogenation of methylesters from rapseed oil using a Palladium catalyst.

Composition and amount of the inlet flow to the reactor:

|  | mole % | weight % | mg/min |
|---|---|---|---|
| propane | 96.27 | 95.7 | 1840 |
| hydrogen | 3.1 | 0.14 | 2.7 |
| FAME | 0.63 | 4.16 | 80 |

Reaction conditions:

| catalyst | 5% Pd on char coal (E101 O/D 5 Degussa AG) |
|---|---|
| reactor volume | 0.007 ml |

-continued

| | |
|---|---|
| reaction time | 80 ms |
| temperature | 90° C. |
| pressure | 70 bar | productivity and product quality:

| | |
|---|---|
| productivity | 700 000 kg FAME/m³ h |
| Iodine-value | reactor inlet = 110 |
| | reactor outlet <1 |
| FAME with trans | <0.1% of all FAME |

Comments

This example shows that a tremendous productivity (700 000 kg FAME/m³ h) can be attained at near-critical conditions. The results above is only an example. We do not claim that it is the optimal conditions for the process.

Example 3

Complete hydrogenation of methylesters from rapeseed oil using a nickel catalyst.

Composition and amount of the inlet flow to the reactor:

| | mole % | weight % | mg/min |
|---|---|---|---|
| propane | 99.49 | 99.13 | 1500 |
| hydrogen | 0.38 | 0.017 | 0.25 |
| FAME | 0.13 | 0.85 | 13 |

Reaction conditions:

| | |
|---|---|
| catalyst | Nickel (Ni-5256 P, Engelhard) |
| reactor volume | 0.009 ml |
| reaction time | 65 ms |
| temperature | 190° C. |
| pressure | 155 bar | productivity and product quality:

| | |
|---|---|
| productivity | 90 000 kg FAME/m³ h |
| Iodine-value | reactor inlet = 110 |
| | reactor outlet <1 |
| FAME with trans | <0.1% of all FAME |

Comments

This example shows that a very high productivity (90 000 kg FAME/m³h) can be attained using a nickel catalyst at super-critical conditions. The results above is only an example. We do not claim that it is the optimal conditions for the process.

Example 4

Complete hydrogenation of triglycerides using a palladium catalyst.

Composition and amount of the inlet flow to the reactor:

| | mole % | weight % | mg/min |
|---|---|---|---|
| propane | 98.7 | 93.6 | 3600 |
| hydrogen | 1 | 0.043 | 1.6 |
| triglycerides | 0.3 | 6.3 | 240 |

The triglycerides (tg) were in this case a commercial vegetable oil.

Reaction conditions:

| | |
|---|---|
| catalyst | 5% Pd on char coal (E 101 O/D 5% Degussa AG |
| reactor volume | 2.5 ml |
| reactor time | 12 sec |
| temperature | 50° C. |
| pressure | 100 bar | productivity and product quality:

| | |
|---|---|
| productivity | 5 000 kg tg/m³ h |
| Iodine-value | reactor inlet = 140 |
| | reactor outlet = 0.1 |
| FA with trans | <0.1% of all FA |

Comments:

This example shows that a high productivity (5000 kg triglycerides/m³h) can be attained at near-critical conditions. The results above is only an example. We do not claim that it is the optimal conditions for the process.

We claim:

1. A process for hydrogenation of a hydrogentable substrate comprising the steps of mixing the substrate, hydrogen gas and a solvent to form a substantially homogeneous solution in a super-critical or near-critical state; and bringing the substantially homogenous solution into contact with a hydrogenation catalyst under conditions of time, temperature and pressure effective to produce hydrogenated substrate as a constituent of the substantially homogeneous solution.

2. A process according to claim 1, wherein the solvent is selected from the group consisting of ethane, ethene, propane, propene, butane, butene, $CO_2$, dimethyl ether, freons, $N_2O$, $N_2$, $NH_3$ and mixtures thereof.

3. A process according to claim 1, wherein the substrate comprises lipids.

4. A process according to claim 1, wherein the solvent comprises a saturated hydrocarbon or an unsaturated hydrocarbon, which results on hydrogenation in a saturated hydrocarbon.

5. A process according to claim 2, wherein the solvent is propane.

6. A process according to claim 1, wherein a noble metal or a nickel catalyst is used for the selective hydrogenation of a substrate containing a carbon-carbon-double bond (C═C).

7. A process according to claim 1, further comprising the steps of determining the iodine number during the formation of hydrogenated substrate and interrupting the reaction when the desired iodine number has been obtained, the desired iodine number being near zero for full hydrogenation and above zero for partial hydrogenation.

8. A process according to claim 1, wherein zinc chromite or any other catalytic salt of zinc is used as a catalyst for the selective hydrogenation of a substrate having the formula COOR to form hydrogenated substrate having the formula C—OH and HO—R.

9. A process according to claim 1, wherein copper chromite, copper free from chrome, or any other catalytic salt of copper is used as a catalyst for the selective hydrogenation of a substrate having the formula COOR to form hydrogenated substrate having the formula C—OH and HO—R or the hydrogenation of a substrate containing carbon-carbon double bonds or for both reactions simultaneously.

10. A process according to claim 1, wherein the substrate comprises oxygen.

11. A process according to claim 10, wherein the solvent is selected from the group consisting of $CO_2$, $N_2$, $NH_3$, and mixtures thereof.

12. A process according to claim 11, wherein the solvent is $CO_2$.

13. A process according to claim 10, wherein a noble metal is used as catalyst for the hydrogenation of oxygen to hydrogen peroxide.

* * * * *

UNITED STATES PATENT AND TRADEMARK OFFICE
CERTIFICATE OF CORRECTION

PATENT NO.  : 5,962,711
DATED       : October 5, 1999
INVENTOR(S) : Magnus Härröd; Poul Møller It is certified that error appears in the above-identified patent and that said Letters Patent is hereby corrected as shown below:

Title page,
Item [75] should read as follows:
-- [75] Inventors: Magnus Härröd , Alingsas, Sweden; Poul Møller, Aarhus, Denmark. --

Signed and Sealed this

Nineteenth Day of February, 2002

*Attest:*

JAMES E. ROGAN
*Attesting Officer*  *Director of the United States Patent and Trademark Office*